United States Patent
Richardson et al.

(10) Patent No.: US 6,391,304 B1
(45) Date of Patent: May 21, 2002

(54) PEPTIDES DERIVED FROM THE ENV GENE OF THE FELINE IMMUNODEFICIENCY VIRUS AND THEIR APPLICATIONS

(75) Inventors: Jennifer Richardson, Orsay; Anne Moraillon, La Varenne Saint Hilaire; Pierre Sonigo; Gianfranco Pancino, both of Paris, all of (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 09/529,377

(22) PCT Filed: Oct. 15, 1998

(86) PCT No.: PCT/FR98/02213

§ 371 Date: May 19, 2000

§ 102(e) Date: May 19, 2000

(87) PCT Pub. No.: WO99/20650

PCT Pub. Date: Apr. 29, 1999

(30) Foreign Application Priority Data

Oct. 17, 1997 (FR) .............................. 97 13042

(51) Int. Cl.$^7$ ................................. A61K 39/21
(52) U.S. Cl. ................. 424/188.1; 424/185.1; 424/186.1; 424/208.1; 530/326; 514/2
(58) Field of Search ...................... 530/326; 424/186.1, 424/185.1, 188.1, 208.1

(56) References Cited

FOREIGN PATENT DOCUMENTS

| EP | 0 577 458 | 1/1994 |
| FR | 2 669 338 | 5/1992 |
| WO | WO93/08836 | 5/1993 |
| WO | WO94/06471 | 3/1994 |

OTHER PUBLICATIONS

Richardson J. et al.: "Neutralization Sensitivity and Accessibility of Continuous B Cell Epitopes of the Feline Immunodeficiency Virus Envelope" *Journal of General Virology*, vol. 77, No. 4, 1966, pp. 759–771, XP002041747, Reading GB.

Richardson J. et al.: "Delayed Infection after Immunization with a Peptide from the Transmembrane Glycoprotein of the Feline Immunodeficiency Virus" *Journal of General Virology*, vol. 72, No. 3, 1998, pp. 2406–2415, XP002094008, American Society for Microbiology US.

*Primary Examiner*—Laurie Scheiner
(74) *Attorney, Agent, or Firm*—Alston & Bird LLP

(57) ABSTRACT

The invention is drawn is to peptides encoded by the feline immunodeficiency virus (FIV) env gene and their immunoprophylactic applications (prevention and treatment of feline immunodeficiency). Said peptides, capable of inducing a certain degree of protection against FIV infection are selected from the group consisting of: peptides containing 12 to 19 amino acids which correspond to the following: Lys-Lys-Gly-Leu-Gln-Gln-Leu-Gln-Glu-Trp-Glu-Asp-Trp-Val -Gly-Trp-Ile-Gly-Asn (SEQ ID NO:1); and peptides of not more than 50 amino acids comprising said sequence set forth by SEQ ID NO:1.

2 Claims, 4 Drawing Sheets

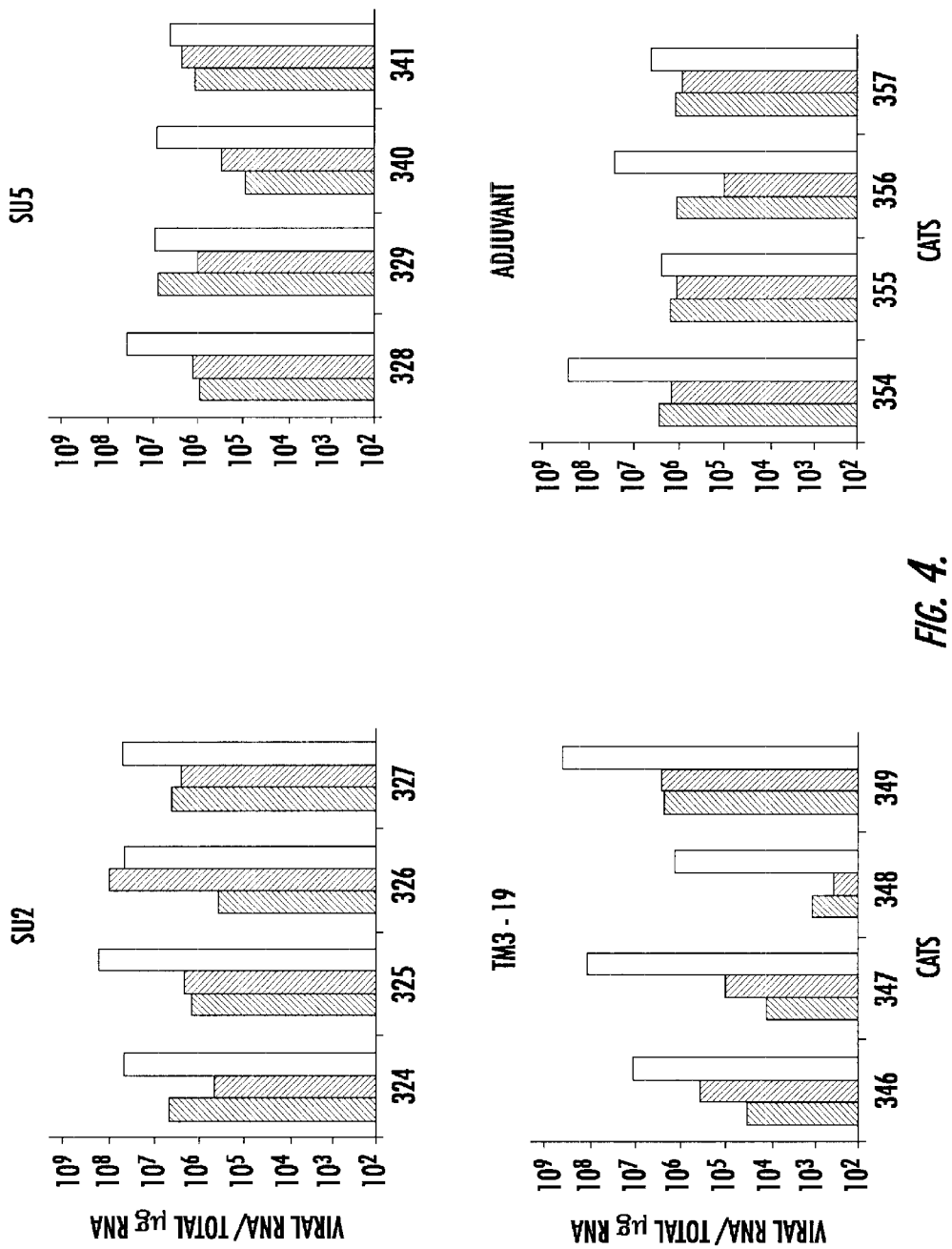

Figure 1:
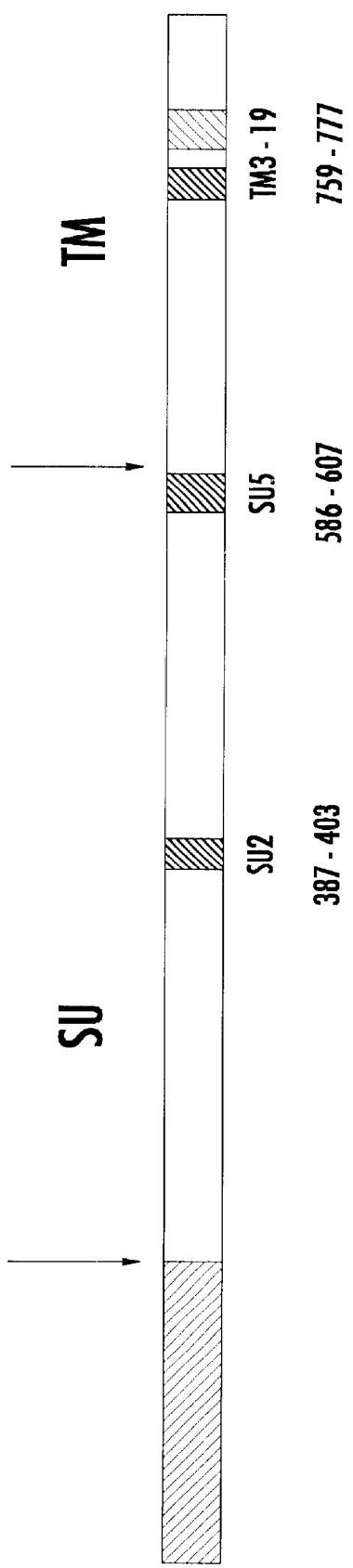

SEQUENCE LISTING

<160> NUMBER OF SEQ ID NOS: 10

<210> SEQ ID NO 1
<211> LENGTH: 19
<212> TYPE: PRT
<213> ORGANISM: Feline immunodeficiency virus

<400> SEQUENCE: 1

Lys Lys Gly Leu Gln Gln Leu Gln Glu Trp Glu Asp Trp Val Gly Trp
 1               5                  10                  15

Ile Gly Asn

<210> SEQ ID NO 2
<211> LENGTH: 17
<212> TYPE: PRT
<213> ORGANISM: Feline immunodeficiency virus

<400> SEQUENCE: 2

Arg Ala Ile Ser Ser Trp Lys Gln Arg Asn Arg Trp Glu Trp Arg Pro
 1               5                  10                  15

Asp

<210> SEQ ID NO 3
<211> LENGTH: 22
<212> TYPE: PRT
<213> ORGANISM: Feline immunodeficiency virus

<400> SEQUENCE: 3

Gln Val Val Lys Gln Pro Asp Tyr Leu Val Val Pro Gly Glu Val Met
 1               5                  10                  15

Glu Tyr Lys Pro Arg Arg
            20

<210> SEQ ID NO 4
<211> LENGTH: 35
<212> TYPE: DNA
<213> ORGANISM: Feline immunodeficiency virus

<400> SEQUENCE: 4
cggggtaccc aatatgtagc acttgaccca aaaat                              35

<210> SEQ ID NO 5
<211> LENGTH: 34
<212> TYPE: DNA
<213> ORGANISM: Feline immunodeficiency virus

<400> SEQUENCE: 5
gctctagatc ttgcttctgc ttgttgttct tgag                               34

<210> SEQ ID NO 6
<211> LENGTH: 34
<212> TYPE: DNA
<213> ORGANISM: Feline immunodeficiency virus

<400> SEQUENCE: 6
ggatgaaagc ttaaagcccc tgatggtcct agac                               34

<210> SEQ ID NO 7
<211> LENGTH: 26
<212> TYPE: DNA
<213> ORGANISM: Feline immunodeficiency virus -continued

```
<400> SEQUENCE: 7
caatatgtag cacttgaccc aaaaat                                          26

<210> SEQ ID NO 8
<211> LENGTH: 26
<212> TYPE: DNA
<213> ORGANISM: Feline immunodeficiency virus

<400> SEQUENCE: 8
tcttgcttct gcttgttgtt cttgag                                          26

<210> SEQ ID NO 9
<211> LENGTH: 26
<212> TYPE: DNA
<213> ORGANISM: Feline immunodeficiency virus

<400> SEQUENCE: 9
ctctgcaaat ttaacaccta ctgaca                                          26

<210> SEQ ID NO 10
<211> LENGTH: 26
<212> TYPE: DNA
<213> ORGANISM: Feline immunodeficiency virus

<400> SEQUENCE: 10
gctgcagtaa aatagggtaa tggtct                                          26
```

PEPTIDES DERIVED FROM THE ENV GENE OF THE FELINE IMMUNODEFICIENCY VIRUS AND THEIR APPLICATIONS

This application is a 371 of PCT/FR98/02213, filed Oct. 15, 1998.

The present invention relates to peptides derived from the env gene of FIV (feline immunodeficiency virus), as well as to their immunoprotective uses (prevention and treatment of feline immunodeficiency).

Feline immunodeficiency is due to a lentivirus, feline immunodeficiency virus (FIV), which has a genetic structure similar to that of the lentiviruses of primates (HIV and SIV).

A certain number of fragments have been selected and have allowed the development of sensitive and specific tests for detecting seropositive animals, as described in European patent applications No. 0 564 477 of Nov. 20, 1991, No. 0 577 458 of Jun. 16, 1993 and French patent application No. 94/07062 of Jun. 9, 1994, in the name of the Applicant, and are mostly derived from the Env protein of FIV, comprising 854 amino acids, the sequence of which is described in European patent application No. 0 577 458.

The Env protein gives, after cleavage, 2 glyco-protein fragments referred to as SU (surface glycoprotein) and TM (transmembrane glycoprotein), in which nine domains, comprising continuous B epitopes of the envelope glycoproteins of the FIVs and recognized during the natural infection (Pancino G. et al., J. Virol, 1993, 67, 664–672), have been defined.

Among these nine domains, five (SU1–SU5) of them are located on the surface glycoprotein and four of them (TM1–TM4) are located on the transmembrane glycoprotein.

More specifically, the positions of the domains TM1–TM4 in the TM protein are as follows:
  the TM1 domain (51 amino acids) corresponds to positions 595–647 of the Env protein of FIV,
  the TM2 domain (31 amino acids) corresponds to positions 681–711 of the Env protein of FIBV; this domain contains an epitope including the sequence: $Cys^{697}$-Asn-Gln-Asn-Gln-Phe-Phe-Cys-$Lys^{705}$ (peptide referred to as P237),
  the TM3 domain (45 amino acids) corresponds to positions 744–788 of the Env protein of FIV, and
  the TM4 domain (29 amino acids corresponds to positions 826–854 of the Env protein of FIV.

Whereas in the field of detection, a set of reagents is now available to detect FIV, in the immunoprotection field, the situation is more complex.

The TM2 peptide, for example, can induce the formation of facilitating antibodies, which have an effect contrary to that which is desired, i.e. an effect of amplifying the viral infection instead of having a protective effect.

In particular, it is observed that vaccination with preparations of FIV envelope entails a clinical aggravation or acceleration of the viral infection.

Although it is usually recognised that the function of antibodies is conventionally estimated by tests of neutralization of the viral infectivity of cells in culture, the results observed have shown that most of the neutralizing antibodies are directed against the envelope glycoproteins, but that a vaccination with the lent iviral envelope, despite the induction of neutralizing antibodies, does not make it possible to obtain a suitable protection with respect to experimental infections (Johnson R. P., Curr. Opinion in Immunol., 1996, 8, 554–560).

In particular, after immunization with the FIV envelope glycoprotein and a virulence test, either a decrease in the viral load (Hosie M. J. et al., Vaccine, 1996, 14, 405–411) or an aggravation of the primary infection (Siebelink K. H. et al., J. Virol., 1995, 69, 3, 3704–3711) was observed in cats. In the latter study (Siebelink K. H. et al., 1995, mentioned above), the aggravation of the infection with FIV is also observed in animals subjected to a passive transfer of plasma from immunized cats; such results suggest the possibility that it is the antibodies which are inducing the increase in the Infection observed IBM vivo.

The possibility of the immune response directed against the FIV envelope being deleterious to the host was confirmed by the Inventors, in a vaccination experiment with the env gene, which led to an acceleration of the infection.

However, both the existence of a causal link between the aggravation of the infection and the presence of antibodies, and the existence of a link between the degree of protection obtained and the presence of antibodies, are difficult to establish and show the complexity encountered for developing compositions that are effectively protective with respect to lentiviruses and more particularly FIV. The reason for this is that he presence of facilitating antibodies in the serum of patients infected with HIV-1 has been correlated, in certain studies, with the progression of the disease (Fust G. et al., AIDS, 1994, 8, 603–609; Hornsy J. et al., J. Virol., 1990, 64, 1437–1440).

It is in particular strongly possible that the antibodies which increase the lentiviral infectivity can also reduce the degree of protective immunity obtained during the natural infection, after vaccination with subunits of envelope protein.

Although the induction of antibodies which neutralise the viral infection in vitro was considered hitherto as a good indicator for selecting sequences capable of inducing a protective immunity, the abovementioned results show that there is in fact no neutralizing activity/protection correlation (Matteuci D. et al., J. Virol., 1996, 70, 617–622)

In addition, the conditions for measuring the activity and the choice of viruses on which the tests are carried out intervene in the interpretation of the results.

Particularly influential parameters which may be mentioned are: the cell substrate used to measure the residual infectivity and the passages of the virus, the use of primary isolates relative to the viruses adapted in the laboratory.

The selection of monoclonal antibodies with strong neutralizing power and directed against conformations epitopes has suggested that discontinuous epitpes are important of the protection. However, the identification and synthesis of mimotopes for vaccinal use are particularly difficult to achieve.

Peptides, representing continuous epitopes, are reagents that are entirely suitable for vaccine purposes. The continuous neutralizing epitope of HIV-1 which has beer, most extensively studied is the main neutralizing domain of the surface glycoprotein, the V3 domain (Goudsmit J. et al., Proc. Natl. Acad. Sci. USA, 1988, 85, 4478–4482; Palker T. J. et al., Proc. Natl. Acad. Sci. USA, 1988, 85, 1932–1936; Rusche J. R. et al., Proc. Natl. Acad. Sci. USA, 988, 85, 3198–3202). However, this region is hypervariable and the neutralization is essentially limited to the homologous virus.

A peptide derived from the V3 region of FIV, which induces neutralizing antibodies, induced no antiviral protection in immunized cats (Lombardi, J. Virol, 1994, 68, 8374–8379). This clearly shows that the in vitro neutralization does not directly signify protective capacity.

Given the complexity of the reactivity of the immune system with respect to lentiviral proteins and the fact that not all the neutralizing antibodies systematically have protective activity, the Inventors set themselves the aim of using synthetic peptides such as those described in European patent application No. 0 577 458 to prepare a medicinal product capable of providing a certain degree of protection against an infection with FIV and of selecting novel synthetic peptides capable of inducing a certain degree of protection against a virulence test with a primary strain of FIV; such a protection is observed by the reduction or suppression of the viral load during the acute infection.

A subject of the present invention is the use of peptides selected from the group consisting of:
  peptides containing from 12 to 19 amino acids and whose sequence is contained in SEQ ID NO:1 below: Lys-Lys-Gly-Leu-Gln-Gln-Leu-Gln-Glu-Trp-Glu-Asp-Trp-Val-Gly-Trp-Ile-Gly-Asn (SEQ ID NO: 1) and
  peptides containing not more than 50 amino acids comprising the said sequence SEQ ID NO:1, to prepare a medicinal product capable of inducing a certain degree of protection against an infection with. FIV.

A subject of the present invention is also peptides capable of inducing a certain degree of protection (preventive or therapeutic) against an infection with FIV, characterized in that they are selected from the group consisting of peptides containing from 12 to 19 amino acids and whose sequence is contained in the sequence SEQ ID NO:1.

The invention includes the analogues of the said peptides in which certain amino acids are substituted, deleted or added, the peptides obtained inducing the same degree of protection with respect to an infection with FIV as that obtained with the peptides as defined above.

Surprisingly, a decrease or an elimination of the viral load is observed during an acute infection, only after immunization with the peptide of SEQ ID NO:1, a fragment thereof comprising at least 12 amino acids or a peptide containing the said sequence SEQ ID NO:1.

The 19-amino-acid peptide of SEQ ID NO:1, also referred to as TM3–19, is a fragment of the peptide corresponding to the TM3 domain.

A systematic analysis of the functional activity of antibodies directed against the various abovementioned domains (SU1–SU5 and TM1–TM4) allowed the identification of only a single domain, SU2, located in the third variable region, as being capable of inducing antibodies wich neutralize the viral infectivity of cells in culture (de Rcnde A. et al., *Virology*, 1994, 198, 257–264; Lombardi S. et al., *J. Virol.*, 1993, 67, 4742–4749; Richardson J. et al., *J. Gen. Virol.*, 1996, 77, 759–771).

Three domains (SU2, SU5 and TM3–19), recognized in the majority of infected cats, were selected by he Inventors as "candidates" as inmunogens. However, although the SU2 domain induces the production of neutralizing antibodies, only the fragment containing the sequence SEQ ID NO:1 is effectively protective with respect to the infection.

Surprisingly, the sequence TM3–19 or sequences of less than 50 amino acids containing it, has protective activity (both preventive and curative), although it does not Induce the production of neutralizing antibodies.

A subject of the present invention is also an immunoprotective and/or vaccinal composition against an infect on with FIV, characterized in that it consists essentially of at least one peptide containing from 12 to 19 amino acids as defined above, optionally combined with another peptide which snows immunoreactivity with respect to anti-FIV antibodies (other viral subunits and/or complete envelope glycoprotein) and which is capable of inducing a certain degree of protection against an infection with FIV, and at least one pharmaceutically acceptable vehicle.

A subject of he present invention is also an immunoprotective composition, as defined above, for its use in the prevention (vaccine) or treatment of injections with FIV.

The evaluation of the viral load of FIV and/or monitoring of the efficacy of the vaccination or of the treatment in a biological sample can be carried out by a method which comprises:
  (a) extraction of the viral RNA from a biological sample to be analysed;
  (b) preparation of a range of samples each containing a different number of a competitive RNA, obtained from a conserved region of the gag gene, into which at least one modification has been introduced;
  (c) mixing of the RNA extract obtained in (a) with each sample of the range obtained in (b), separately
  (d) reverse transcription of the RNAs present in the various mixtures obtained in (c), to give the corresponding cDNA;
  (e) amplification of the cDNAs obtained in (d), using primers selected from the group consisting of the sequences SEQ ID NO:7, SEQ ID NO:8, SEQ ID NO:9 and SEQ ID NO:10;
  (f) separation of the amplification products, and
  (g) detection of the number of copies of initial viral RNA by suitable quantitative analysis, such as comparative densitometry and establishment of the ratio: density of products from the competitive RNA/density of products from the wild-type RNA present in the initial sample, as a function of the number of copies of competitive RNA added to each mixture.

The competitive RNA according to step (b) is obtained, when the said modification is a deletion, by:
  (i) amplification of the said conserved region using primers of sequence SEQ ID NO:4 and SEQ ID NO:5,
  (ii) execution of the deletion by mutagenesis via PCR of the 3' portion of the product obtained in (i), using primers of sequence SEQ ID NO:6 and SEQ ID NO:5,
  (iii) replacement of the terminal 3' portion of the product obtained in (i) with the fragment bearing the deletion obtained in (ii), and
  (iv) production of the said competitive RNA using the final product obtained in (iii) as matrix.

Figure 2:
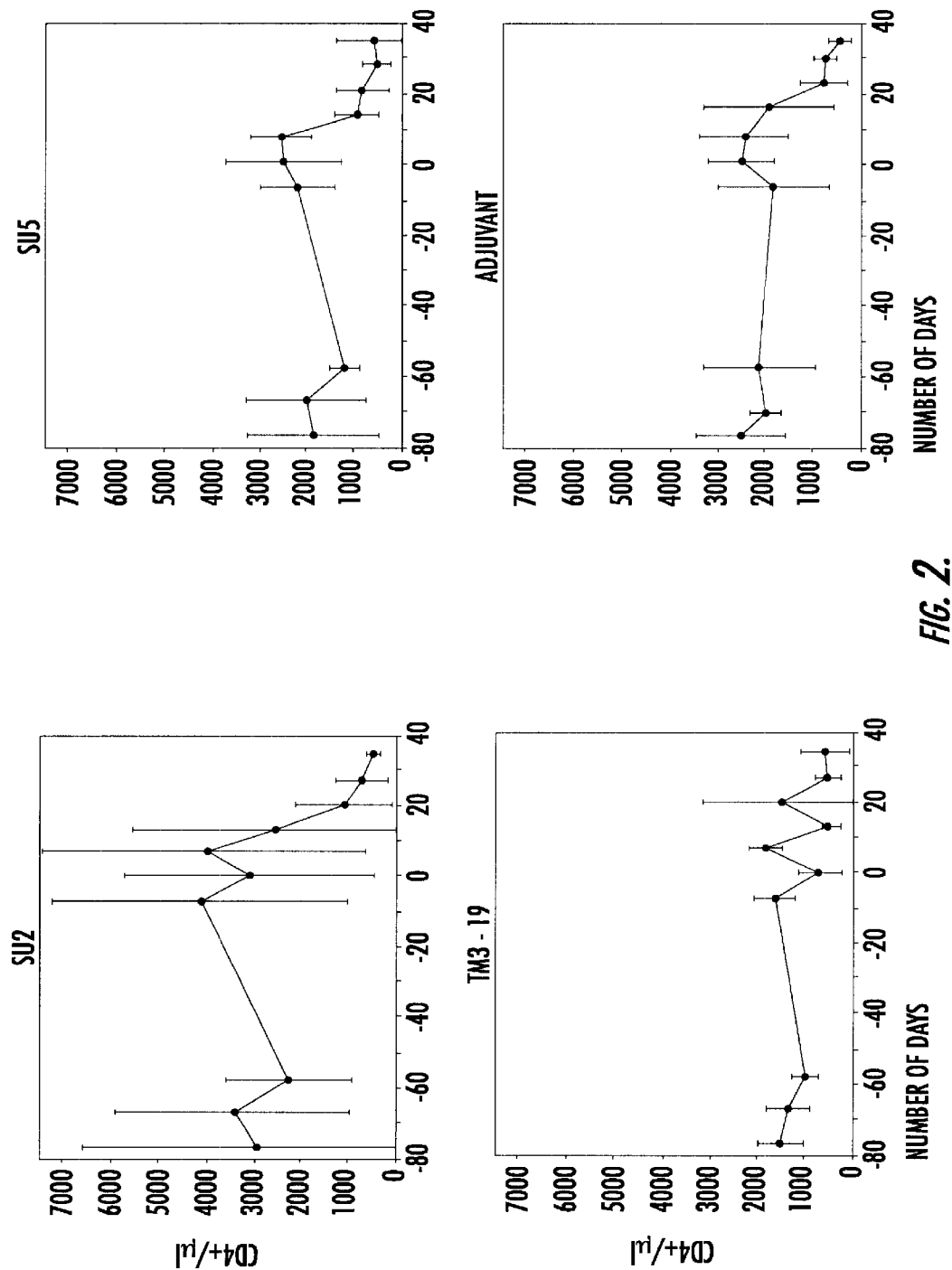
Figure 3:
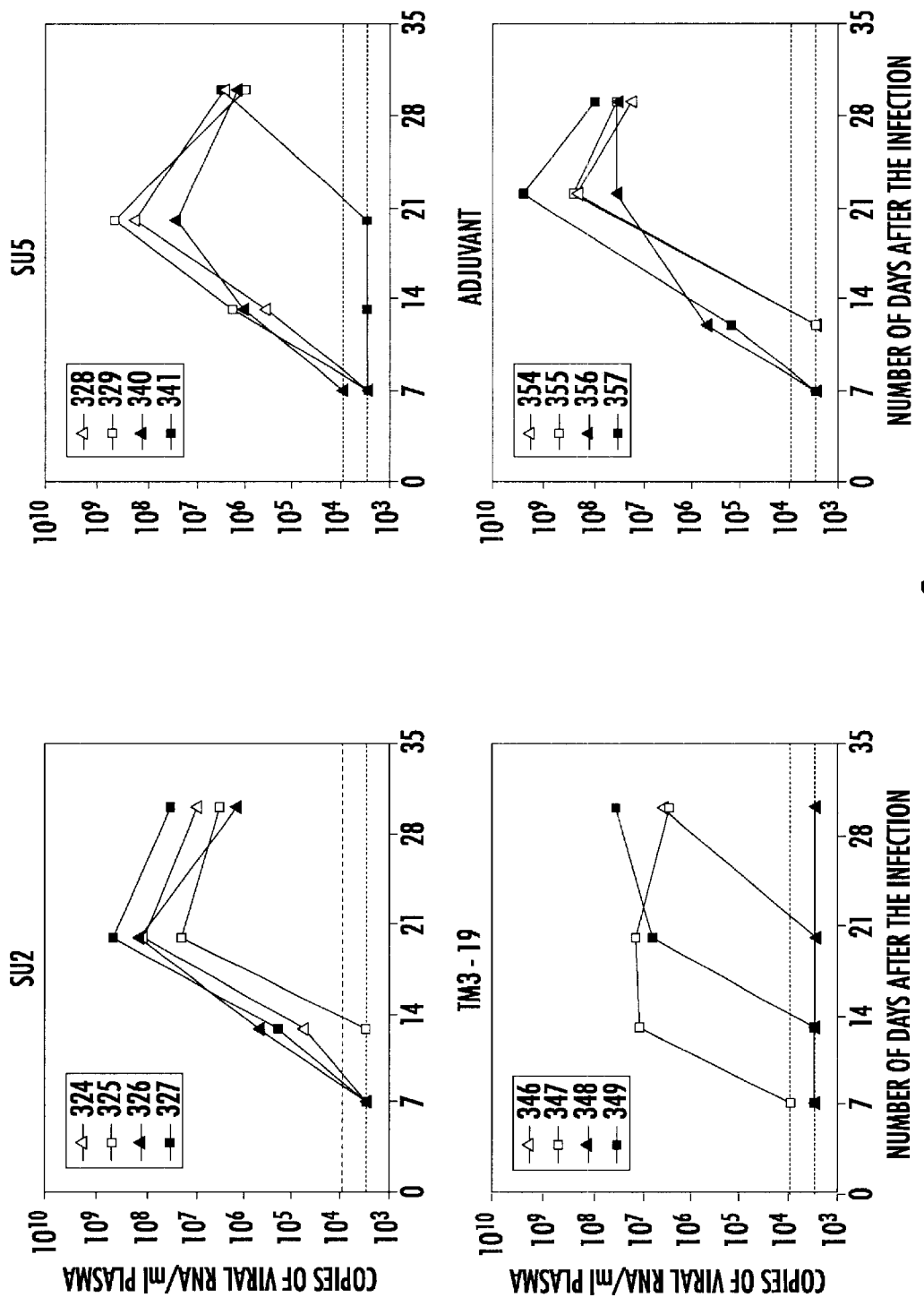

Besides the preceding arrangements, the invention also comprises other arrangements, which will emerge from the description hereinbelow, which refers to examples of implementation of the process which is the subject of the present invention, as well as to the attached drawings, in which:

FIG. 1 is a diagrammatic representation of the surface (SU) and transmembrane (TM) envelope glycoproteins of FIV. The peptides SU2, SU5 and TM3–19 (-■-) are used as immunogens. The proteolytic cleavage sites which remove the signal peptide (◆) and which generate the mature envelope glycoproteins (↓) are indicated. The positions correspond to those of the envelope glycoproteins of the wild-type strain Wo. The zone -□- corresponds to the intermembrane domain; the zone -□- corresponds to the signal peptide;

FIG. 2 corresponds to an analysis of the lymphocyte subsets. The number of circulating $CD4^-$ lymphocytes is expressed in the form of an average value, during the immunization and after the virulence test, during the acute infection;

FIG. 3 illustrates the viral load in the plasma during the primary infection. The viral load, determined by RT-PCR, is expressed with the aid of the number of copies of viral RNA/ml of plasma (y-axis) as a function of the number of days (x-axis). The line as discontinuous hyphens corresponds to plasmas in which the viral RNA, although detected, is present at values of less than 30 copies/reaction (⊲580 copies/ml of plasma); the dotted line corresponds to the detection threshold (⊲2860 copies/ml of plasma);

FIG. 4 illustrates the viral load in the tissues. It is expressed as the number of copies of viral RNA/total µg of RNA (y-axis), for each cat. It is determined by RT-PCR. The results obtained are illustrated for the axillary ganglia (■), the spleen (□) and the thymus (□).

It should be clearly understood, however, that these examples are given purely for the purposes of illustrating the subject of the invention, of which they do not in any way constitute a limitation.

EXAMPLE 1

Materials and Methods used to Illustrate the Protective Activity of the Peptides According to the Invention 1. Tissue Culture The clone ID 10 (Osborne R., *J. Gen. Virol.*, 1994, 75, 3641–3645) of Crandell's feline kidney fibroblasts (Crandeil's feline kidney cells or CrFK) is cultured in DMEM medium (Dulbecco's modified Eagle's medium) supplemented with 10% heat-inactivated foetal calf serum (FCS), 100 IU/ml of penicillin and 100 µ/ml of streptomycin. The feline T-lymphoid cell line FL-4 (Yamamoto J. et al., *Intervirology*, 1991, 32, 361–375), which is given a chronic infection with the Petaluma strain of FIV (Pedersen N. C. et al., *Science*, 1987, 235, 790–793), is cultured in an RPMI-1640 medium supplemented with FCS and the above-mentioned antibiotics (complete RPMI medium).

Feline peripheral blood mononuclear cells (or PBM cells) are isolated from the blood of noninfected cats, by density-gradient centrifugation and activated for 3 days in a complete RPMI medium containing 5 µ/l of concanavalin A, 50 µM of 2-mercaptoethanol (2-ME) and 10 mM of HEPES.

2. Viruses

The Petaluma and Wo isolates (Pedersen N. C. et al., *Science*, 1987, 235, 790–793) (Moraillon A. et al., *Vet. Microbiol.*, 1992, 31; 41–54) of FIV are obtained, respectively, from supernatants of the FL-4 cell line and from infected feline PBM cells. The Wo isolate was subjected to a limited number of passages, only on the mononuclear cells (PBMC).

3. Peptides

Peptides are included in the envelope glycoprotein domains defined previously as containing continuous B epitopes (Pancino G. et al., *J. Virol.*, 1993, 67, 664–672).

They have The sequences given in the sequence listing in accordance with the table below:

| | |
|---|---|
| SU2 | SEQ ID NO: 2 |
| SU5 | SEQ ID NO: 3 |
| TM3-19 (759–777) | SEQ ID NO: 1 |

The position of these peptides in the env sequence is illustrated in FIG. 1. The numbering corresponds to that in the Wo sequence (Pancino et al., *Virology*, 1993, 192, 659–662).

4. Immunization and Virulence test

Groups of four cats 4½ months old are immunized subcutaneously with 120 µg of FIV peptide (approximately 250 µg of peptide coupled to KLH (keyhole limpet haemocyanin)), emulsified in complete Freund's adjuvant.

Four repeat immunizations are administered subcutaneously in an incomplete Freund's adjuvant, generally at intervals of 2–3 weeks, although the interval between the last 2 infections was 7 weeks.

Four cats which have been subjected to the same protocol of subcutaneous injections, with an adjuvant only, are used as negative control.

The development of the immune response is monitored regularly.

The cats are subjected to a virulence test, one week after the final immunization, by means of an intraperitoneal inoculation of 10 $CID_{50}$ of FIV Wo isolate, one $CID_{50}$ corresponding to the dose capable of infecting 50% of the cats.

The following tests are carried out on the blood collected each week: counting of the $CD4^+$ T lymphocytes, isolation of the virus, determination of the viral RNA in the plasma (competitive PT-PCP) and serological analyses.

The cats are sacrificed five weeks after the virulence test. The lymphoid organs (spleen, thymus, axial lymphatic ganglia) are recovered and frozen in liquid nitrogen, for extraction of the RNA.

5. Serological Analyses

The production on of antibodies is evaluated before the test by means of an ELISA using an immobilized peptide (SU2, SU5, TM2 or TM3-19) and immunoprecipitation. After the test, the seroconversion is monitored by an ELISA using immobilized envelope peptides and a recombinant FTV capsid protein.

6. ELISA

The ELISA with the immobilized envelope peptides corresponding to the immunogenic domains SU2 and TM2 and with the immobilized recombinant p25 protein (FIV capsid protein) is carried out as described in Avraméas A. et al. (*Res. Virol.*, 1993, 144, 209–218).

Microplates (Immunolon II, Dynatech) are coated with 0.5 µg/well for the peptides and with 0.1 µg/well for the p25 protein.

The tests are carried out in duplicate and the results are expressed as average values.

The anti-peptide titres before the test are expressed as the logarithm of the inverse of the last dilution of serum which gives an absorbance (at 405 nm) of greater than 0.1.

After the test, the seroconversion against the envelope peptides and the p25 protein is evaluated at serum dilutions of ¹⁄25 and ¹⁄100, respectively.

The absorbance values (at 405 nm) are corrected by subtraction of the absorbance values obtained by binding with an immobilized control peptide.

The tests are normalized with reference to the binding of a mixture of serum from cats infected with FIV with a peptide representing the immunodominant domain of the FIV transmembrane glycoprotein (TM2) (Avraméas A. et al., *Res. Virol.*, 1993, 144, 209–218).

7. Immunoprecipitation

The sera collected on the day of the test (at a dilution of ¹⁄40) are used to immunoprecipitate the envelope glycoproteins derived from the metabolically labelled FL-4 cells and feline mononuclear cells (PBM cells) infected with the FIV Wo strain, as described in G. Pancino et al. (*Virology*, 1995, 206, 796–806).

8. Tests of Neutralization and Reduction of Viral Infectivity

The detection of antibodies neutralizing the infection of the CrFKs with the FIV Petaluma strain is carried out as described previously (Richardson J. et al., *J. Gen. Virol.*, 1996, 77, 759–771).

For the test of reduction of the viral infectivity, serial dilutions (1/50, 1/100, 1/200 and 1/400) of a stock suspension of Wo isolate and a single dilution of serum (1/5) are prepared in a complete RPMI medium containing 50 μM of 2-ME and 10 mM of HEPES.

The feline serum is mixed with an equal volume of the serial dilutions of virus and incubated in a final volume of 100 μl for one hour at 37° C.

The concentration of PBM cells activated with a mitogen is adjusted to $4\times10^6$/ml in a complete RPMI medium comprising 2-ME, HEPES and 200 U/ml of recombinant human IL-2. 0.1 ml of cell suspension ($4\times10^5$ cells) is added to the tubes.

After incubation overnight, the viral inoculum is recovered by washing the cells twice with 0.5 ml of complete RPMI medium.

The cells are then resuspended fin 0.2 ml of feline serum diluted in a complete RDMI medium comprising 2-ME, HEPES and 100 U/ml of IL-2, and then transferred into the wells of 96-well microtitration plates.

Half of the medium is replaced four days after the infection.

10 μl aliquots are recovered 7 days after the infection, for an analysis of the reverse transcriptase activity.

9. Analysis of the Lymphocyte Subsets

Counting of the $CD4^+$ T lymphocytes is carried out at regular intervals before the test, on the day of the test and at regular intervals during the acute infection.

The $CD4^+$ T lymphocytes are counted by flow cytometry, using monoclonal antibodies (Clinisciences).

10. Isolation of the Virus

The plasmatic viraemia is quantified by culturing PBM cells (Ho D. D. et a., *N. Engl. J. Med.*, 1989, 321, 1621–1625).

The infection is estimated by determining the p25 by ELISA (Petcheck, IDEXX) in culture supernatants, obtained 14 and 21 days after the inoculation of different volumes of plasma (0.2, 2, 10, 40, 200 or 1000 μl). The final plasmatic dilution giving a positive culture is considered as the limit point.

The plasmatic viraemia is expressed as $TCDID_{50}$/ml of plasma (→doses capable of infecting 50% of the tissue cultures).

11. Preparation of the RNA

Plasmatic RNA

The plasma is filtered (0.45 μm) and the RNA not associated with cells is extracted directly from the filtered plasma using the Viral RNA kit (Qiagene) and eluted in 50 μl of water according to the manufacturer's instructions, and the RNA is then divided into aliquots and stored at −80° C.

Tissue RNA

Frozen spleen and thymus tissues are reduced to powder and immediately dispersed in the lysis buffer provided with the RNA extraction kit (RNeasy, Qiagene), with the aid of a tissue homogenizer (Ultra-Turrax). The frozen axillary lymphatic ganglia are dispersed directly in the lysis buffer; the RNA is then extracted using the RNeasy kit, according to the manufacturer's instructions.

The contaminant DNA is removed by hydrolysis with DNase 1 (RQ1. RNase-free DNase, Promega).

12. Competitive RT-PCR

A conserved region of the FIV gag gene is selected as a target sequence for the reverse transcription of the competitive RNA and the overlapping PCR amplification.

Amplification of the native target sequence gives a 312-base-pair initial product and a 165-base-pair overlapping product, corresponding to nucleotides 1059–1370 and to nucleotides 1157–1321 of the FIV 34TF10 clone (Taibott R. L. et al., *Proc. Natl. Acad. Sci.* USA, 1989, 86, 5743–5747).

Molecular Constructs

The 312-base-pair target sequence is amplified using a plasmid (pKSgag) containing all of the gag gene of the FIV Wo strain (Pancino G. et al., *Virology*, 1993, 67, 664–672), using as 5' primer the sequence SEQ ID NO:4 (SKWoG107), comprising the 5' sequence of the target matrix and a KpnI site, and as 3' primer the sequence SEQ ID NO:5 (RXWoG139), which comprises the 3' sequence of the target matrix and an XbaI site, under the same conditions as those outlined below to obtain the sequence modified by deletion.

The amplification product is sub-cloned into the corresponding sites of the pBluescript KS+ plasmid, thus giving the plasmid pBSQCgag.

To prepare a matrix for the synthesis of the competitive RNA, 31 nucleotides are deleted in the gag sequence, by PCR.

The 3' portion of the native sequence is amplified using a 5' primer, SHΔWoG128 (SEQ ID NO:6), complementary to the natural HindIII site (nucleotides 1241–1246) and containing a discontinuity of 31 nucleotides, and a 3' primer RXWoG139 (SEQ ID NO:5), comprising the 3' sequence of the target matrix and an XbaI site, under the following conditions: the native sequence (10 ng of pBSQCgag) is amplified in a final volume of 100 μl containing 2.5 mM of $MgCl_2$, 200 μM of dNTP, 1× of commercial buffer and 2.5 U of Taq polymerase (GibcoBRL) and each primer at 0.2 μM. The DNA is denatured at 94° C. for 3 minutes, subjected to 30 cycles of amplification (94° C. 30 s/55° C. 30 s/72° C. 30 s) and subjected to an elongation at 72° C. for 7 minutes, in the presence of the primers for the sequences SEQ ID NO:6 and SEQ ID NO:5.

The amplification product is purified, digested with the HindIII and XbaI enzymes and substituted with the corresponding fragment of pBSQCgag, giving the plasmid pBSQCΔgag.

Synthesis of the Competitive RNA

The competitive RNA is synthesized from the transcription product of the plasmid pBSQCΔgag linearized with XbaI, using T3 RNA polymerase (Proméga Gemini kit).

The DNA matrix is hydrolysed with RQ1 Rnase-free DNase (Proméga). The competitive RNA is purified by absorption on silica (Rneasy, Quagène) and quantified by measuring the absorbance at 260 nm. The RNA is divided into aliquots and stored at −80° C.

Competitive RT-PCR

For the synthesis of the cDNA, 2.5 μl of viral RNA are mixed with 2.5 μl containing different numbers of copies of competitive RNA; typically, the various samples of competitive RNA are prepared using 5 semi-logarithmic dilutions, straddling the number of copies estimated in the biological sample.

The RNA is denatured at 65° C. for 5 minutes and immediately placed on ice. The reagents for the reverse transcription (15 µl) are added.

The final reaction mixtures contain 0.3 U/ml of random hexanucleotides (sequences of 6 randomly aligned nucleotides which make it possible theoretically to amplify any RNA fragment) (Pharmcia), 0.5 mM of dNTP, 10 mM of DTT, 1× of commercial buffer (Gibco BRL) and 100 U of Superscript II (Glbco BRL), in a volume of 20 µl.

The reactions are first carried out at 25° C. for 10 minutes to promote the hybridization of the primers, and then at 42° C. for 50 minutes. The reverse transcriptase is inactivated by incubation at 95° C. for 5 minutes.

As control, all the RNA samples are also amplified directly by PCR to check the complete removal of any DNA which may be present in the biological sample.

The highly conserved sequences are selected as primers. The complementary DNA is amplified by overlapping PCR, using:

as external primers:
SWoG107 5'-CAATATGTAGCACTTGACCCAAAAAT-3' (1059–1084; SEQ ID NO:7) and RWoG139 5'-TCTTGCTTCTGCTTGTTGTTCTTCAG-3' (1370–1345; SEQ ID NO:8) and as internal primers:
SWoG116 5'-CTCTGCAAATTTAACACCTACTGACA-3' (1157–1182); SEQ ID NO:9) and RWoG133 5'-GCTGCAGTAAAATAGGGTAATGGTCT-3' (1321–1296; SEQ ID NO:10).

For the first amplification, the PCR reagents (80 µl) are added as a mixture with 20 µl of cDNA.

More specifically, the reaction mixture contains: 200 µM of dNTP, 1.5 mM of MgCl$_2$, 0.1 µM of each external primer, 0.8× of commercial buffer (Gibco BRL) and 0.25 U of Taq polymerase.

The DNA is denatured at 94° C. for 3 minutes, subjected to 28 cycles of amplification (94° C. 30 s/55° C. 30 s/72° C. 30 s) and to an elongation at 72° C. for 7 minutes.

For the overlapping amplification, 2 µl of the product of the first amplification is transferred into 98 µl of reaction mixture containing 200 µM of dNTP, 1.5 mM of MgCl$_2$, 0.5 µM of each internal primer, 1× of commercial buffer (Gibco BRL) and 0.25 U of Taq polymerase (Gibco BRL).

The DNA is denatured at 94° C. for 3 minutes, subjected to 28 cycles of amplification (94° C. 30 s/52° C. 30 s/72° C. 30 s) and to an elongation at 72° C. for 7 minutes.

Analysis

The amplification products (10 µl) are subjected to electrophoresis on 2.75% agarose gel.

Digital images of the gels stained with ethidium bromide are obtained using the Appligene Imager and the densitometry analyses are carried out with the Image NIH software. The density of the competitive product is adjusted as a function of the difference between the length of the native sequence and that of the competitive sequence.

The logarithm of the ratio:density or competitive product/density of the native product, is plotted as a function of the logarithm of the number of copies of competitive RNA added to each reaction.

The best adjustment is determined by the least-squares method and the number of copies of native RNA corresponds to the intersection of the axis of the Xs (Piatak M. Jr. et al., *Biotechniques*, 1993, 14, 70–80).

13. Statistical Analysis

The cumulative area under the curve (Dawson J., *Drug Information J.*, 1994, 28, 723–732) is calculated from graphs illustrating the ratio: copies of viral RNA/ml of plasma/time, and compared with the Mann-Whitney test.

EXAMPLE 2

Evaluation of the Humoral Response Obtained with TM3–19 and its Protective Effects 1. Development of a Humoral Response to Envelope Peptides.

To evaluate the effect of the humoral immunity with respect to particular domains of the envelope glycoproteins during a primary infection with FIV, cats are immunized with peptides (FIG. 1) corresponding to the envelope domains comprising the continuous B epitopes recognized during the natural infection.

All the immunized cats develop a strong antibody response, as determined by ELISA with envelope peptides used as immunogens.

The results of these ELISA assays are summarized in Table I below:

TABLE I

Antibody response during the immunization

| | | Anti-peptide titre[a] | | | Immuno-precipitation[b] |
|---|---|---|---|---|---|
| | Cats | 1st injection | 2nd injection | Day of the test | Day of the test |
| SU2 | 324 | 4.71 | 5.01 | 5.61 | + |
| | 325 | 5.01 | 5.31 | 5.01 | + |
| | 326 | 4.40 | 4.71 | 5.31 | − |
| | 327 | 5.31 | 5.01 | 4.71 | + |
| SU5 | 328 | 5.01 | 5.31 | 4.71 | + |
| | 329 | 5.31 | 5.31 | 5.01 | + |
| | 340 | 4.71 | 5.01 | 5.01 | + |
| | 341 | >5.61 | 5.31 | 5.01 | + |
| TM3-19 | 346 | 4.71 | 4.71 | 4.40 | + |
| | 347 | 5.01 | 5.31 | 4.71 | + |
| | 348 | 5.31 | 5.01 | 4.40 | − |
| | 349 | nd | 3.20 | 4.40 | − |

[a]titre expressed as the logarithm of the inverse of the last dilution of serum for which the absorbance at 405 nm is greater than 0.1.
[b]immunoprecipitation of the envelope glycoproteins using metabolically labelled FL-4 cells (groups SU2 and SU5) or infected PBM cells (group TM3-19).

On the day of the test, the titres, expressed as the logarithm of the inverse of the serum dilution, are between 4.40 and 5.61.

The recognition of the envelope glycoproteins is estimated by immunoprecipitation of the biosynthetically labelled envelope glycoprotein with sera collected on the day of the test, as summarized in Table I.

The sera from all the cats immunized with the SU5 peptide and and 3 of the 4 cats (324, 325 and 327) immunized with the SU2 peptide immunoprecipitate the envelope glycoproteins of the Petaluma strain obtained from lysates of chronically infected FL-4 cells.

Given that the TM3–19 peptide, deduced from the Env sequence of the FIV Wo strain, comprises 4 different residues out of 19, relative to the Petaluma sequence, the capacity to immunoprecipitate sera before the test of the cats immunized with the TM3–19 peptide was tested against the envelope glycoproteins of the Wo strain, obtained from PBM cell lysates after acute infection with the FIV Wo strain.

Whereas only the sera of 2 cats (346, 347) immunized with the TM3–19 peptide precipitate the envelope protein of the Wo strain, the immunoprecipitation of the viral envelope is less efficient using acutely infected PBM cells than using chronically infected lymphoblastoid cell lines.

2. Activity of the Antibodies Directed Against the Envelope Peptides in a Biological Test To evaluate the function of the antibodies, the feline sera directed against the SU2 peptide are tested for their neutralizing value with respect to the infection of CrFK cells with the FIV Petaluma strain.

Only one cat (327) immunized with the SU2 peptide develops neutralizing antibodies: the final dilution which reduces the infection by at least 50% is $1/160$.

The sera from cats immunized with the SU5 and TM3–19 peptides do not neutralize the FIV Petaluma strain (measurement in the CrFK cell line).

On account of the diversity of the sequence of the envelope glycoproteins for the Petaluma and Wo strains, and in particular in the TM3 domain, the functional activity of the antibodies was also studied in a homologous test.

Given that the Wo strain was not adapted by passage on CrFK cells, the influence of the antibodies was studied on the infection in feline PBMC cells.

In a test of reduction of infectivity using PBMC cells activated with a mitogen, the sera directed against the SU2 and TM3–19 peptides do not modify the infection with FIV Wo, despite the neutralizing activity observed for one of the sera directed against the SU2 peptide, when CrFK cells are used as cell substrate.

3. Isolation of the FIV After the Virulence Test

After the test, all the cats are infected, as determined by isolation of the FIV virus in PBM cells, after inoculation of the plasma collected, 2 and 3 weeks after the test.

4. Seroconversion After the Virulence Test

After testing with the FIV Wo strain, most of the cats show a humoral response with respect to the viral components, as illustrated by the ELISA with the SU2 and TM2 peptides, derived from the external and transmembrane glycoproteins, respectively, and the recombinant capsid protein.

The results are illustrated in Table II below.

TABLE II

Binding of the sera to the viral components as a function of time (weeks) after the virulence test[a]

| Cats Group | Cat No. | SU2[b] 3 | 4 | 5 | TM2 3 | 4 | 5 | p25 3 | 4 | 5 |
|---|---|---|---|---|---|---|---|---|---|---|
| SU2 | 324 | — | — | — | 0 | 2.1 | 2.5 | 0 | 0.2 | 1.9 |
|  | 325 | — | — | — | 0 | 1.4 | 2.1 | 0 | 0 | 0.2 |
|  | 326 | — | — | — | 0 | 1.3 | 2.1 | 0 | 0.2 | 1.1 |
|  | 327 | — | — | — | 0 | 2.2 | 2.3 | 0 | 0.4 | 1.3 |
| SU5 | 328 | 0 | 1.9 | 2.4 | 2.3 | 2.9 | 3.0 | 0.1 | 2.7 | 2.9 |
|  | 329 | 0 | 0.5 | 0.7 | 0 | 2.8 | 3.1 | 0 | 1.0 | 2.2 |
|  | 340 | 0 | 0 | 0.1 | 0.1 | 2.4 | 2.8 | 0 | 0.2 | 0.8 |
|  | 341 | 0 | 0 | 0 | 0 | 0 | 0 | 0 | 0 | 0 |
| TM3-19 | 346 | 0 | 0 | 0 | 0 | 0.1 | 1.9 | 0 | 0.1 | 0.6 |
|  | 347 | 0 | 0 | 0 | 1.2 | 2.4 | 2.5 | 0.2 | 2.3 | 2.3 |
|  | 348 | 0 | 0 | 0 | 0 | 0 | 0 | 0 | 0 | 0 |
|  | 349 | 0 | 0 | 0 | 0 | 0.5 | 2.3 | 0.1 | 0 | 0.1 |
| Adjuvant | 354 | 0 | 2.4 | 3.0 | 0 | 2.6 | 3.0 | 0 | 0 | 2.6 |
|  | 355 | 0 | 0.2 | 0.2 | 0.1 | 2.3 | 3.1 | 0 | 0.1 | 2.0 |
|  | 356 | 0.4 | 0.3 | 0.3 | 2.2 | 3.0 | 3.1 | 0 | 0.5 | 1.4 |
|  | 357 | 0 | 0.2 | 1.0 | 0.2 | 2.9 | 3.1 | 0 | 0.9 | 2.5 |

[a]data obtained by ELISA carried out with the SU2 and TM2 envelope peptides and the p25 recombinant FIV capsid protein for seral dilutions of 1/25 (peptides) and of 1/100 (p25); these data are expressed as optical density (see Example 1);
[b]data not illustrated for the group of cats vaccinated with SU2 (seropositive before the virulence test).

The development of an antiviral humoral response is weaker and retarded in 3 cats (346, 348, 349) immunized with the TM3–19 peptide, in comparison with the response of the control cats, although the last cat (347) of this group developed a strong and rapid antibody response.

5 weeks after the test, none of the cats immunized with the TM3–19 peptide developed a detectable antibody response with respect to the SU2 peptide, although the control cats show detectable responses.

Whereas, at 4 weeks, most (11/12) of the cats immunized with the SU2 and SU5 peptides and the cats which received only the adjuvant developed a large response against the TM2 peptide, all but one (347) of the cats immunized with the TM3–19 peptide show a weak or undetectable response.

Whereas, at 5 weeks, all the control cats respond well to the p25 protein, one cat (348) immunized with the TM3–19 peptide does not respond and among the other 3 cats, 2 animals (346, 349) develop only weak responses.

5. Haematological Modifications During the Acute Infection

To evaluate the effect of the immunization on the pathology associated with a primary infection, circulating $CD4^+$ lymphocytes are counted before and after the test with the FIV Wo strain.

The number of $CD^+$ lymphocytes is illustrated in FIG. 2.

Although the tendencies are masked by an individual heterogeneity, most of the cats immunized with the SU2 and SU5 peptides and the cats which received only the adjuvant show a gradual reduction in the number of $CD4^+$ lymphocytes after the infection (FIG. 2).

Despite a certain degree of fluctuation, the number of $CD4^+$ lymphocytes does not show a large decrease like that observed in the other groups during the acute infection in the cats of the TM3–19 group (FIG. 2).

6. Plasmatic Viral Load Determined by RT-PCR

Given that it could not be expected to obtain an appreciable immunity by vaccination with only one domain of the envelope glycoproteins, it was necessary to develop a quantitative method for evaluating the viral load which should allow the detection of modest reductions, but having a particularly large significance, of the viral dissemination.

Accordingly, the Inventors developed a competitive RT-PCR which allowed the quantitative determination of the viral RNA in the plasma and tissues.

This test allows the detection of 10 copies of RNA, during a reaction, which establishes the lower limit for detection at 1430 copies of RNA/ml of plasma when the viral RNA is extracted from 140 µl of plasma.

After the test with 10 $CID_{50}$ of Wo isolate, the viral RNA can be detected in the plasma by RT-PCR two weeks after the infection.

In the cats which received only adjuvant, a peak in the number of copies of viral RNA is observed at three weeks, which car be up to $2.5 \times 10^9$ copies/ml of plasma (FIG. 3).

The presence of antibodies directed against a domain known to induce neutralizing antibodies, SU2, before the test does not appear to modify the course of the primary infection.

Among the cats immunized with the SU5 peptide, the acute infection of 3 cats followed kinetics similar to those of the control cats, while infection in one of the cats appears in a retarded manner.

The course of the infection in the cats immunized with the TM3–19 peptide is generally different from that observed with the control cats.

Although the infection in one of the cats (347) appears rapidly, the infection in the other 3 cats of this group appears in a retarded manner.

In addition, it was not possible to detect a plasmatic viraemia in one of the cats (348) during the measurement period.

The number of copies of viral RNA observed in the cats immunized with the TM3–19 peptide never exceeds $3.1\times\mathbf{10}^6$ copies/ml, which indicates a significant reduction relative to the viraemia observed in the group of control cats.

These data were analysed, comparing the area under the cumulative curve (Dawson J. D., *Drug Information J.,* 1994, 28, 723–732) at 3 and 4 weeks after the test.

With the Mann-Whitney test, the reduction in the viral load observed in the cats immunized with the TM3–19 relative to the control cats is significant both at 3 weeks and 4 weeks ($p=0.02$).

7. Phasmatic Viraemia

For the cats immunized with the TM3–19 peptide and the control cats, the plasmatic viral load is evaluated 3 weeks after the test by isolating the virus.

The number of copies of viral RNA determined by competitive RT-PCR is compared with the plasmatic viraemia determined by culturing PBM cells.

The results are illustrated in Table III below.

TABLE III

| Cats | | Plasmatic viraemia RT-PCR[α] | Plasmatic viraemia PBMC culture[β] |
|---|---|---|---|
| TM3-19 | 346 | undetectable | 1 |
| | 347 | $1.19 \times 10^7$ | $1 \times 10^2$ |
| | 348 | undetectable | 1 |
| | 349 | $5.56 \times 10^6$ | 1 |
| Adjuvant | 354 | $1.93 \times 10^8$ | $5 \times 10^3$ |
| | 355 | $2.43 \times 10^8$ | $5 \times 10^2$ |
| | 356 | $3.12 \times 10^7$ | $5 \times 10^3$ |
| | 357 | $2.54 \times 10^9$ | $5 \times 10^4$ |

[α]The plasmatic viraemia is measured by competitive RT-PCR and expressed as a number of copies of viral RNA/ml of plasma.
[β]The plasmatic viraemia is measured by culturing PBM cells and expressed as $TCID_{50}$/ml of plasma.

Immunization with the TM3–19 peptide before the virulence test results in a large reduction (about 3 logs) in the level of infectious virus in the plasma, of three-quarters of the cats, very early in the course of the primary infection.

These data confirm that the reduced levels of viral RNA observed for the cats immunized with the TM3–19 peptide in comparison with those obtained with the control cats clearly reflect the reduction in the plasmatic titre of the infectious virus.

8. Viral Load in the Tissues Determined by Competitive RT-PCR

The viral load in the tissues is evaluated 5 weeks after the test by counting the number of copies of viral RNA in the axillary lymphatic ganglia and in the thymus by competitive RT-PCR.

Given that the amplified fragment (amplicon) is located in the intron of the sub-genomic viral RNA, the copies of viral RNA counted in the tissues represent the complete transcripts, which are either intracellular or encapsidated in the extracellular viral particles.

The viral RNA is detected in all he tissues examined and in all the cats (FIG. 4).

The levels of viral RNA in the axillary lymphatic ganglia are lower in three cats (346, 348 and 349) immunized with the TM3–19 peptide than in the cats immunized with the SU2 and SU5 peptides and the control cats.

In the spleen, the level of viral RNA is particularly low in one cat (348) immunized with the TM3–19 peptide.

However, in the thymus, the viral load is similar in the four groups of cats, and, in general, it is higher than in the other tissues examined.

A high viral load in the thymus at an early stage of the infection was also observed by in situ hybridization (Beebe A. M. et al., *J. Virol.,* 1994, 68, 3080–3091).

It is not possible to know whether or not the apparent larger infection of the thymus reflects (i) its richness in cells preferentially infected at the start of infection, (ii) a large capacity to trap the viral particles, or (iii) the sequential nature of the colonization (tissues examined before the resolution of the acute infection).

These results show that although the immunization with two peptides derived from the surface glycoprotein (SU2 and SU5) do not modify the course of the infection, immunization with the TM3–19 peptide derived from the extracellular membrane proximal domain of the transmembrane glycoprotein significantly retards the viral dissemination.

These results also show that the induction of antibodies which neutralize the viral infection in vitro does not necessarily have a good correlation with the desired immune protection.

In particular, the neutralizing activity/protection correlation is problematic, especially given that the activity measured depends on the conditions of the test used and more particularly on the cell substrate used to measure the residual infectivity.

In point of fact, the neutralization of the primary lentiviral isolates is fundamentally different from the neutralization of the virus adapted to propagation in cell cultures.

The results obtained with the peptides according to the invention also show that they significantly retard the infection.

As emerges from the disclosure hereinabove, the invention is not limited in any way to those of its modes of implementation, preparation or application which have just been described more explicitly; on the contrary, it encompasses any variant which may occur to a person skilled in the art, without departing from the context or scope of the present invention.

What is claimed is:

1. A medicinal product capable of inducing protection in a feline host against an infection with Feline Immunodeficiency virus (FIV), comprising peptides selected from the group consisting of (i) isolated peptides containing the sequence: Lys-Lys-Gly-Leu-Gln-Gln-Leu-Gln -Glu-Trp-Glu-Asp-Trp-Val-Gly-Trp-Ile-Gly-Asn (SEQ ID NO:1) and (ii) the isolated peptide set forth by SEQ ID NO:1.

2. An isolated peptide capable of inducing protection in a feline host against an infection with FIV, characterized in that said peptide consists essentially of the sequence set forth by SEQ ID NO:1.

* * * * *